United States Patent
Racie et al.

(10) Patent No.: US 6,689,599 B1
(45) Date of Patent: Feb. 10, 2004

(54) AGGRECANASE MOLECULES

(75) Inventors: Lisa A. Racie, Acton, MA (US); Natalie C. Twine, Goffstown, NH (US); Michael J. Agostino, Andover, MA (US); Neil Wolfman, Dover, MA (US); Elisabeth A. Morris, Southboro, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 09/981,953

(22) Filed: Oct. 18, 2001

Related U.S. Application Data

(60) Provisional application No. 60/242,317, filed on Oct. 20, 2000.

(51) Int. Cl.$^7$ .............................. C12N 9/64; C12N 5/00; C12P 21/06; C07H 21/04; C07K 1/00

(52) U.S. Cl. ...................... 435/226; 435/325; 435/69.1; 435/219; 536/23.2; 530/350

(58) Field of Search ................................ 435/219, 322, 435/69.1, 226; 536/23.2; 530/350

(56) References Cited

U.S. PATENT DOCUMENTS 4,419,446 A   12/1983   Howley et al. ............... 435/68

FOREIGN PATENT DOCUMENTS

| EP | 0 123 289 A2 | 10/1984 |
|---|---|---|
| EP | 0 155 476 A1 | 9/1985 |
| EP | 0 177 343 A1 | 4/1986 |
| WO | WO 86/00639 | 1/1986 |
| WO | WO 01/11074 A2 | 2/2001 |
| WO | WO 01/23561 | 4/2001 |
| WO | WO2000183782 A2 * | 11/2001 |

OTHER PUBLICATIONS

Abbaszade, Ilgar, et al., "Cloning and Characterization of ADAMTS11, an Aggrecanase from the ADAMTS Family," *J. Biol. Chem.*, 274(33), 1999, pp. 23443–23450.

Flannery, Carl R., et al., "Identification of a Stromelysin Cleavage Site within the Interglobular Domain of Human Aggrecan," *J. Biol. Chem.*, 267(2), 1992, pp. 1008–1014.

Fosang, Amanda J., "Neutrophil collagenase (MMP–8) cleaves at the aggrecanase site $E^{373}$–$A^{374}$ in the interglobular domain of cartilage aggrecan," *Biochem. J.*, 304, 1994, pp. 347–351.

Gething, Mary–Jane, et al., "Cell–surface expression of influenza haemagglutinin from a cloned DNA copy of the RNA gene," *Nature*, 293, 1981, pp. 620–625.

Gough, Nicholas M., et al., "Structure and expression of the mRNA for murine granulocyte–macrophage colony stimulating factor," *The EMBO Journal*, 4(3), 1985, pp. 645–653.

Hughes, Clare E., et al., "Monoclonal antibodies that specifically recognize neoepitope sequences generated by 'aggrecanase' and matrix metalloproteinase cleavage of aggrecan: application to catabolism in situ and in vitro," *Biochem. J.*, 305, 1995, pp. 799–804.

Jang, Sung K., et al., "Initiation of Protein Synthesis by Internal Entry of Ribosomes into the 5' Nontranslated Region of Encephalomyocarditis Virus RNA In Vivo," *J. of Virology*, 63(4), 1989, pp. 1651–1660.

Kaufman, Randal J., et al., "Amplification and Expression of Sequences Cotransfected with a Modular Dihydrofolate Reductase Complementary DNA Gene," *J. Mol. Biol.*, 159, 1982, pp. 601–621.

Kaufman, Randal J., et al., "Coamplification and Coexpression of Human Tissue–Type Plasminogen Activator and Murine Dihydrofolate Reductase Sequences in Chinese Hamster Ovary Cells," *Mol. Cell. Biol.*, 5(7), 1985, pp. 1750–1759.

Kaufman, Randal J., et al., "Construction of a Modular Dihydrofolate Reductase cDNA Gene: Analysis of Signals Utilized for Efficient Expression," *Mol. Cell. Biol.*, 2(11), 1982, pp. 1304–1319.

Kaufman, Randal J., "Identification of the components necessary for adenovirus translational control and their utilization in cDNA expression vectors," *Proc. Natl. Acad. Sci. USA*, 82, 1985, pp. 689–693.

Kaufman, Randal J., et al., "Improved vectors for stable expression of foreign genes in mammalian cells by use of the untranslated leader sequence from EMC virus," *Nucleic Acids Research*, 19(16), 1991, pp. 4485–4490.

Laemmli, U.K., "Cleavage of Structural Proteins during the Assembly of the Head of Bacteriophage T4," *Nature*, 227, 1970, pp. 680–685.

Lohmander, J. Stefan, et al., "The Structure of Aggrecan Fragments in Human Synovial Fluid: Evidence that Aggrecanase Mediates Cartilage Degradation in Inflammatory Joint Disease, Joint Injury, and Osteoarthritis," *Arthritis & Rheumatism*, 36(9), 1993, pp. 1214–1222.

Maniatis, T., et al., *Molecular Cloning: A Laboratory Manual*, Cold Spring Harbor Laboratory, 1982, pp. 387–389.

Mercuri, Francesca A., et al., "Recombinant Human Aggrecan G1–G2 Exhibits Native Binding Properties and Substrate Specificity for Matrix Metalloproteinases and Aggrecanase," *J. Biol. Chem.*, 274(45), 1999, pp. 32387–32395.

Miller, David W., et al., "An Insect Baculovirus Host–Vector System for High–Level Expression of Foreign Genes," *Genetic Engineering: Principles and Methods*, 8, 1986, pp. 277–298.

(List continued on next page.)

Primary Examiner—Rebecca E. Prouty
Assistant Examiner—Malgorzata Walicka

(57) ABSTRACT

Aggrecanase proteins and the nucleotides sequences encoding them as well as processes for producing them are disclosed. Methods for developing inhibitors of the aggrecanase enzymes and antibodies to the enzymes for treatment of conditions characterized by the degradation of aggrecan are also disclosed.

2 Claims, No Drawings

OTHER PUBLICATIONS

Oakley, Berl R., et al., "A Simplified Ultrasensitive Silver Stain for Detecting Proteins in Polyacrylamide Gels," *Analytical Biochemistry*, 105, 1980, pp. 361–363.

Okayama, Hiroto, et al., "High–Efficiency Cloning of Full-Length cDNA," *Molecular and Cellular Biology*, 2(2), 1982, pp. 161–170.

Sandy, John D., et al., "Catabolism of Aggrecan in Cartilage Explants," *J. Biol. Chem.*, 266(14), 1991, pp. 8683–8685.

Sandy, John D., et al., "The Structure of Aggrecan Fragments in Human Synovial Fluid: Evidence for the involvement in Osteoarthritis of a Novel Proteinase Which Cleaves the Glu 373–Ala 374 Bond of the Interglobular Domain," *J. Clin. Invest.*, 89, 1992, pp. 1512–1516.

Taniguchi, Tadatsugu, et al., "Expression of the human fibroblast interferon gene in *Escherichia coli*," *Proc. Natl. Acad. Sci. USA*, 77(9), 1980, pp. 5230–5233.

Tortorella, M.D., et al., "Purification and Cloning of Aggrecanase–1: A Member of the ADAMTS Family of Proteins," *Science*, 284, 1999, pp. 1664–1666.

Towbin, Harry, et al., "Electrophoretic transfer of proteins from polyacrylamide gels to nitrocellulose sheets: Procedure and some applications," *Proc. Natl. Acad. Sci. USA*, 76(9), 1979, pp. 4350–4354.

Apte, S.S., "ADAM–TS10: A Novel Member of the ADAM–TS Family Containing Multiple Thrombospondin Type 1 Repeats," Abstract, XP–002208327, submitted to EMBL/GenBank/DDBJ databases on Jun. 29, 1999.

Hurskainen, Tina L., et al., "ADAM–TS5, ADAM–TS6, and ADAM–TS7, Novel Members of a New Family of Zinc Metalloproteases," *The Journal of Biological Chemistry*, 274(36):25555–25563 (1999).

Shimkets, R.A., et al., "Novel Polynucleotides Encoding Proteins Containing Thrombospondin Type 1 Repeats," Abstract of WO 01/23561 (Apr. 5, 2001).

* cited by examiner

AGGRECANASE MOLECULES

This application claims the benefit of U.S. Provisional Application No. 60/242,317 filed Oct. 20, 2000.

The present invention relates to the discovery of nucleotide sequences encoding novel aggrecanase molecules, the aggrecanase proteins and processes for producing them. The invention further relates to the development of inhibitors of, as well as antibodies to the aggrecanase enzymes. These inhibitors and antibodies may be useful for the treatment of various aggrecanase-associated conditions including osteoarthritis.

BACKGROUND OF THE INVENTION

Aggrecan is a major extracellular component of articular cartilage. It is a proteoglycan responsible for providing cartilage with its mechanical properties of compressibility and elasticity. The loss of aggrecan has been implicated in the degradation of articular cartilage in arthritic diseases. Osteoarthritis is a debilitating disease which affects at least 30 million Americans (MacLean et al. *J Rheumatol* 25:2213–8. (1998)). Osteoarthritis can severely reduce quality of life due to degradation of articular cartilage and the resulting chronic pain. An early and important characteristic of the osteoarthritic process is loss of aggrecan from the extracellular matrix (Brandt, K D. and Mankin H J. *Pathogenesis of Osteoarthritis*, Textbook of Rheumatology, W B Saunders Company, Philadelphia, Pa. pgs. 1355–1373. (1993)). The large, sugar-containing portion of aggrecan is thereby lost from the extra-cellular matrix, resulting in deficiencies in the biomechanical characteristics of the cartilage.

A proteolytic activity termed "aggrecanase" is thought to be responsible for the cleavage of aggrecan thereby having a role in cartilage degradation associated with osteoarthritis and inflammatory joint disease. Work has been conducted to identify the enzyme responsible for the degradation of aggrecan in human osteoarthritic cartilage. Two enzymatic cleavage sites have been identified within the interglobular domain of aggrecan. One ($Asn^{341}$-$Phe^{342}$) is observed to be cleaved by several known metalloproteases (Flannery, C R et al. *J Biol Chem* 267:1008–14. 1992; Fosang, A J et al. *Biochemical J*. 304:347–351. (1994)). The aggrecan fragment found in human synovial fluid, and generated by IL-1 induced cartilage aggrecan cleavage is at the $Glu^{373}$-$Ala3^{74}$ bond (Sandy, J D, et al. *J Clin Invest* 69:1512–1516. (1992); Lohmander L S, et al. *Arthritis Rheum* 36: 1214–1222. (1993); Sandy J D et al. *J Biol Chem*. 266: 8683–8685. (1991)), indicating that none of the known enzymes are responsible for aggrecan cleavage in vivo.

Recently, identification of two enzymes, aggrecanase-1 (ADAMTS 4) and aggrecanase-2(ADAMTS-11) within the "Disintegrin-like and Metalloprotease with Thrombospondin type 1 motif" (ADAM-TS) family have been identified which are synthesized by IL-1 stimulated cartilage and cleave aggrecan at the appropriate site (Tortorella M D, et al. *Science* 284:1664–6. (1999); Abbaszade, I, et al. *J Biol Chem* 274: 23443–23450. (1999)). It is possible that these enzymes could be synthesized by osteoarthritic human articular cartilage. It is also contemplated that there are other, related enzymes in the ADAM-TS family which are capable of cleaving aggrecan at the $Glu^{373}$-$Ala3^{74}$ bond and could contribute to aggrecan cleavage in osteoarthritis.

SUMMARY OF THE INVENTION

The present invention is directed to the identification of aggrecanase protein molecules capable of cleaving aggrecanase, the nucleotide sequences which encode the aggrecanase enzymes, and processes for the production of aggrecanases. These enzymes are contemplated to be characterized as having proteolytic aggrecanase activity. The invention further includes compositions comprising these enzymes as well as antibodies to these enzymes. In addition, the invention includes methods for developing inhibitors of aggrecanase which block the enzyme's proteolytic activity. These inhibitors and antibodies may be used in various assays and therapies for treatment of conditions characterized by the degradation of articular cartilage.

The nucleotide sequence of the aggrecanase molecule of the present invention is set forth in SEQ ID NO: 3. In another embodiment, the nucleotide sequence of the aggrecanase molecule of the present invention is set forth SEQ ID NO: 1 from nucleotide #1 to #3766. In another embodiment the nucleotide sequence of the invention comprises nucleotide #1086(TCG) to #3396(CGC) of SEQ ID NO: 1. The invention further includes equivalent degenerative codon sequences of the sequences set forth in SEQ ID NO: 1, as well as fragments thereof which exhibit aggrecanase activity.

The amino acid sequence of an isolated aggrecanase molecule of the invention comprises the sequence set forth in SEQ ID NO: 4. The amino acid sequence of an isolated aggrecanase molecule comprises the sequence set forth in SEQ ID NO: 2. The invention further includes fragments of the amino acid sequence which encode molecules exhibiting aggrecanase activity.

The human aggrecanase protein or a fragment thereof may be produced by culturing a cell transformed with a DNA sequence of SEQ ID NO: 3 or SEQ ID NO: 1 comprising nucleotide #1 to #3766 of SEQ ID NO: 1 or comprising nucleotide #1086 to #3396 of SEQ ID NO: 1 and recovering and purifying from the culture medium a protein characterized by the amino acid sequence set forth in SEQ ID NO: 4 or SEQ ID NO: 2, respectively, substantially free from other proteinaceous materials with which it is co-produced. For production in mammalian cells, the DNA sequence further comprises a DNA sequence encoding a suitable propeptide 5' to and linked in frame to the nucleotide sequence encoding the aggrecanase enzyme.

The invention includes methods for obtaining additional aggrecanase molecules, the DNA sequence obtained by this method and the protein encoded thereby. The method for isolation of the full length sequence involves utilizing the aggrecanase sequence set forth in SEQ ID NO: 3 or SEQ ID NO: 1 from nucleotide #1086 to #3396 to design probes for screening using standard procedures known to those skilled in the art.

It is expected that other species have DNA sequences homologous to human aggrecanase enzyme. The invention, therefore, includes methods for obtaining the DNA sequences encoding other aggrecanase molecules, the DNA sequences obtained by those methods, and the protein encoded by those DNA sequences. This method entails utilizing the nucleotide sequence of the invention or portions thereof to design probes to screen libraries for the corresponding gene from other species or coding sequences or fragments thereof from using standard techniques. Thus, the present invention may include DNA sequences from other species, which are homologous to the human aggrecanase protein and can be obtained using the human sequence. The present invention may also include functional fragments of the aggrecanase protein, and DNA sequences encoding such functional fragments, as well as functional fragments of other related proteins. The ability of such a fragment to function is determinable by assay of the protein in the biological assays described for the assay of the aggrecanase protein.

The aggrecanase proteins of the present invention may be produced by culturing a cell transformed with the DNA sequence of SEQ ID NO: 3 or SEQ ID NO: 1 comprising nucleotide #1 to #3766 of SEQ ID NO: 1 or comprising nucleotide #1086 to #3396 of SEQ ID NO: 1 and recovering and purifying aggrecanase protein from the culture medium. In one embodiment the protein comprises amino acid sequence of SEQ ID NO: 4 or amino acid #1 to #770 of SEQ ID NO: 2. The purified expressed protein is substantially free from other proteinaceous materials with which it is co-produced, as well as from other contaminants. The recovered purified protein is contemplated to exhibit proteolytic aggrecanase activity cleaving aggrecan. Thus, the proteins of the invention may be further characterized by the ability to demonstrate aggrecan proteolytic activity in an asssay which determines the presence of an aggrecan-degrading molecule. These assays or the development thereof is within the knowledge of one skilled in the art. Such assays may involve contacting an aggrecan substrate with the aggrecanase molecule and monitoring the production of aggrecan fragments (see for example, Hughes et al., *Biochem J* 305: 799–804(1995); Mercuri et al., *J. Bio Chem.* 274:32387–32395 (1999)).

In another embodiment, the invention includes methods for developing inhibitors of aggrecanase and the inhibitors produced thereby. These inhibitors prevent cleavage of aggrecan. The method may entail the determination of binding sites based on the three dimensional structure of aggrecanase and aggrecan and developing a molecule reactive with the binding site. Candidate molecules are assayed for inhibitory activity. Additional standard methods for developing inhibitors of the aggrecanase molecule are known to those skilled in the art. Assays for the inhibitors involve contacting a mixture of aggrecan and the inhibitor with an aggrecanase molecule followed by measurement of the aggrecanase inhibition, for instance by detection and measurement of aggrecan fragments produced by cleavage at an aggrecanase susceptible site.

Another aspect of the invention therefore provides pharmaceutical compositions containing a therapeutically effective amount of aggrecanase inhibitors, in a pharmaceutically acceptable vehicle. Aggrecanase-mediated degradation of aggrecan in cartilage has been implicated in osteoarthritis and other inflammatory diseases. Therefore, these compositions of the invention may be used in the treatment of diseases characterized by the degradation of aggrecan and/or an upregulation of aggrecanase. The compositions may be used in the treatment of these conditions or in the prevention thereof.

The invention includes methods for treating patients suffering from conditions characterized by a degradation of aggrecan or preventing such conditions. These methods, according to the invention, entail administering to a patient needing such treatment, an effective amount of a composition comprising an aggrecanase inhibitor which inhibits the proteolytic activity of aggrecanase enzymes.

Still a further aspect of the invention are DNA sequences coding for expression of an aggrecanase protein. Such sequences include the sequence of nucleotides in a 5' to 3' direction illustrated in SEQ ID NO: 1 comprising nucleotide #1 to #3766 or comprising nucleotide #1086 to #3396 of SEQ ID NO: 1 or SEQ ID NO: 3 and DNA sequences which, but for the degeneracy of the genetic code, are identical to the DNA sequence of SEQ ID NO: 1 and SEQ ID NO: 3, and encode an aggrecanase protein. Further included in the present invention are DNA sequences which hybridize under stringent conditions with the DNA sequence of SEQ ID NO: 1 and SEQ ID NO: 3 and encode a protein having the ability to cleave aggrecan. Preferred DNA sequences include those which hybridize under stringent conditions (see, T. Maniatis et al., *Molecular Cloning* (A Laboratory Manual), Cold Spring Harbor Laboratory (1982), pages 387 to 389. It is generally preferred that such DNA sequences encode a polypeptide which is at least about 80% homologous, and more preferably at least about 90% homologous, to the sequence of set forth in SEQ ID NO: 3 or SEQ ID NO: 1 comprising nucleotide #1 to #3766 or comprising nucleotide #1086 to #3396 of SEQ ID NO: 1. Finally, allelic or other variations of the sequences of SEQ ID NO: 1 or SEQ ID NO: 3, whether such nucleotide changes result in changes in the peptide sequence or not, but where the peptide sequence still has aggrecanase activity, are also included in the present invention. The present invention also includes fragments of the DNA sequence shown in SEQ ID NO: 1 which encode a polypeptide which retains the activity of aggrecanase.

The DNA sequences of the present invention are useful, for example, as probes for the detection of mRNA encoding aggrecanase in a given cell population. Thus, the present invention includes methods of detecting or diagnosing genetic disorders involving the aggrecanase, or disorders involving cellular, organ or tissue disorders in which aggrecanase is irregularly transcribed or expressed. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing an aggrecanase protein of the invention in which a cell line transformed with a DNA sequence encoding an aggrecanase protein in operative association with an expression control sequence therefor, is cultured in a suitable culture medium and an aggrecanase protein is recovered and purified therefrom. This process may employ a number of known cells both prokaryotic and eukaryotic as host cells for expression of the polypeptide. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection.

Still a further aspect of the invention are aggrecanase proteins or polypeptides. Such polypeptides are characterized by having an amino acid sequence including the sequence illustrated in SEQ ID NO: 2 or 4, variants of the amino acid sequence of SEQ ID NO: 2 or 4, including naturally occurring allelic variants, and other variants in which the protein retains the ability to cleave aggrecan characteristic of aggrecanase molecules. Preferred polypeptides include a polypeptide which is at least about 80% homologous, and more preferably at least about 90% homologous, to the amino acid sequence shown in SEQ ID NO: 2 or 4. Finally, allelic or other variations of the sequences of SEQ ID NO: 2 or 4, whether such amino acid changes are induced by mutagenesis, chemical alteration, or by alteration of DNA sequence used to produce the polypeptide, where the peptide sequence still has aggrecanase activity, are also included in the present invention. The present invention also includes fragments of the amino acid sequence of SEQ ID NO: 2 or 4 which retain the activity of aggrecanase protein.

The purified proteins of the present inventions may be used to generate antibodies, either monoclonal or polyclonal, to aggrecanase and/or other aggrecanase-related proteins, using methods that are known in the art of antibody production. Thus, the present invention also includes antibodies to aggrecanase or other related proteins. The antibodies may be useful for detection and/or purification of aggrecanase or related proteins, or for inhibiting or preventing the effects of aggrecanase. The aggrecanase of the invention or portions thereof may be utilized to prepare antibodies that specifically bind to aggrecanase.

DETAILED DESCRIPTION OF THE INVENTION

The human aggrecanase of the present invention comprises the nucleotide sequence set in SEQ ID NO: 3. In another embodiment, the human aggrecanase of the present invention comprises nucleotides #1 to #3766 or nucleotides #1086 to #3396 of SEQ ID NO: 1. The human aggrecanase protein sequence comprises the amino acid sequence set forth in SEQ ID NO: 4. In another embodiment, the human aggrecanase protein sequence comprises amino acids #1 to #770 set forth in SEQ ID NO: 2. Further sequences of the aggrecanase of the present invention may be obtained using the sequences of SEQ ID NO: 3 or SEQ ID NO: 1 comprising nucleotides #1086 to #3396 to design probes for screening for the full sequence using standard techniques.

The aggrecanase proteins of the present invention, include polypeptides comprising the amino acid sequence of SEQ ID NO: 2 or SEQ ID NO: 4 and having the ability to cleave aggrecan.

The aggrecanase proteins recovered from the culture medium are purified by isolating them from other proteinaceous materials from which they are co-produced and from other contaminants present. The isolated and purified proteins may be characterized by the ability to cleave aggrecan substrate. The aggrecanase proteins provided herein also include factors encoded by the sequences similar to those of SEQ ID NO: 3 or the sequence of SEQ ID NO: 1 comprising nucleotide #1 to #3766 or comprising nucleotide #1086 to #3396 of SEQ ID NO: 1, but into which modifications or deletions are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO: 2 or SEQ ID NO: 4. These sequences, by virtue of sharing primary, secondary, or tertiary structural and conformational characteristics with aggrecanase molecules may possess biological properties in common therewith. It is know, for example that numerous conservative amino acid substitutions are possible without significantly modifying the structure and conformation of a protein, thus maintaining the biological properties as well. For example, it is recognized that conservative amino acid substitutions may be made among amino acids with basic side chains, such as lysine (Lys or K), arginine (Arg or R) and histidine (His or H); amino acids with acidic side chains, such as aspartic acid (Asp or D) and glutamic acid (Glu or E); amino acids with uncharged polar side chains, such as asparagine (Asn or N), glutamine (Gln or Q), serine (Ser or S), threonine (Thr or T), and tyrosine (Tyr or Y); and amino acids with nonpolar side chains, such as alanine (Ala or A), glycine (Gly or G), valine (Val or V), leucine (leu or L), isoleucine (Ile or I), proline (Pro or P), phenylalanine (Phe or F), methionine (Met or M), tryptophan (Trp or W) and cysteine (Cys or C). Thus, these modifications and deletions of the native aggrecanase may be employed as biologically active substitutes for naturally-occurring aggrecanase and in the development of inhibitors other polypeptides in therapeutic processes. It can be readily determined whether a given variant of aggrecanase maintains the biological activity of aggrecanase by subjecting both aggrecanase and the variant of aggrecanase, as well as inhibitors thereof, to the assays described in the examples.

Other specific mutations of the sequences of aggrecanase proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of aggrecanase-related protein will also result in production of a non-glycosylated protein, even if the glycosylation sites are left unmodified.

The present invention also encompasses the novel DNA sequences, free of association with DNA sequences encoding other proteinaceous materials, and coding for expression of aggrecanase proteins. These DNA sequences include those depicted in SEQ ID NO: 1 or 3 in a 5' to 3' direction and those sequences which hybridize thereto under stringent hybridization washing conditions (for example, 0.1×SSC, 0.1% SDS at 65° C.; see, T. Maniatis et al., *Molecular Cloning* (*A Laboratory Manual*), Cold Spring Harbor Laboratory (1982), pages 387 to 389) and encode a protein having aggrecanase proteolytic activity. These DNA sequences also include those which comprise the DNA sequence of SEQ ID NO: 1 and those which hybridize thereto under stringent hybridization conditions and encode a protein which maintain the other activities disclosed for aggrecanase.

Similarly, DNA sequences which code for aggrecanase proteins coded for by the sequences of SEQ ID NO: 1 comprising nucleotide #1 to #3766 or comprising nucleotide #1086 to #3396 of SEQ ID NO: 1 or the sequence of SEQ ID NO: 3 or aggrecanase proteins which comprise the amino acid sequence of SEQ ID NO: 2 or 4, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 3 or SEQ ID NO: 1 comprising nucleotide #1 to #3766 or comprising nucleotide #1086 to #3396 of SEQ ID NO: 1 which are caused by point mutations or by induced modifications (including insertion, deletion, and substitution) to enhance the activity, half-life or production of the polypeptides encoded are also encompassed in the invention.

Another aspect of the present invention provides a novel method for producing aggrecanase proteins. The method of the present invention involves culturing a suitable cell line, which has been transformed with a DNA sequence encoding a aggrecanase protein of the invention, under the control of known regulatory sequences. The transformed host cells are cultured and the aggrecanase proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293:620–625 (1981), or alternatively, Kaufman et al., *Mol. Cell. Biol.*, 5(7): 1750–1759 (1985) or Howley et al., U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method. For expression of the protein in bacterial cells, DNA encoding the propeptide of Aggrecanase is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al., *Genetic Engineering*, 8:277–298 (Plenum Press 1986) and references cited therein.

Another aspect of the present invention provides vectors for use in the method of expression of these novel aggrecanase polypeptides. Preferably the vectors contain the full novel DNA sequences described above which encode the novel factors of the invention. Additionally, the vectors contain appropriate expression control sequences permitting expression of the aggrecanase protein sequences. Alternatively, vectors incorporating modified sequences as described above are also embodiments of the present invention. Additionally, the sequence of SEQ ID NO: 3 or SEQ ID NO: 1 or other sequences encoding aggrecanase proteins could be manipulated to express composite aggrecanase molecules. Thus, the present invention includes chimeric DNA molecules encoding an aggrecanase protein comprising a fragment from SEQ ID NO: 3 or SEQ ID NO: 1 comprising nucleotide #1 to #3766 or comprising nucleotide #1086 to #3396 of SEQ ID NO: 1 linked in correct reading frame to a DNA sequence encoding another aggrecanase polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

Various conditions such as osteoarthritis are known to be characterized by degradation of aggrecan. Therefore, an aggrecanase protein of the present invention which cleaves aggrecan may be useful for the development of inhibitors of aggrecanase. The invention therefore provides compositions comprising an aggrecanase inhibitor. The inhibitors may be developed using the aggrecanase in screening assays involving a mixture of aggrecan substrate with the inhibitor followed by exposure to aggrecan. The compositions may be used in the treatment of osteoarthritis and other conditions exhibiting degradation of aggrecan.

The invention further includes antibodies which can be used to detect aggrecanase and also may be used to inhibit the proteolytic activity of aggrecanase.

The therapeutic methods of the invention includes administering the aggrecanase inhibitor compositions topically, systemically, or locally as an implant or device. The dosage regimen will be determined by the attending physician considering various factors which modify the action of the aggrecanase protein, the site of pathology, the severity of disease, the patient's age, sex, and diet, the severity of any inflammation, time of administration and other clinical factors. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known factors, to the final composition, may also effect the dosage.

Progress can be monitored by periodic assessment of disease progression. The progress can be monitored, for example, by x-rays, MRI or other imaging modalities, synovial fluid analysis, and/or clinical examination.

The following examples illustrate practice of the present invention in isolating and characterizing human aggrecanase and other aggrecanase-related proteins, obtaining the human proteins and expressing the proteins via recombinant techniques.

EXAMPLES

Example 1

Isolation of DNA

Potential novel aggrecanase family members were identified using a database screening approach. Aggrecanase-1 (*Science* 284:1664–1666 (1999) has at least six domains: signal, propeptide, catalytic domain, disintegrin, tsp and c-terminal. The catalytic domain contains a zinc binding signature region, TAAHELGHVKF (SEQ ID NO: 5) and a "MET turn"which are responsible for protease activity. Substitutions within the zinc binding region in the number of the positions still allow protease activity, but the histidine (H) and glutamic acid (E) residues must be present. The thrombospondin domain of Aggrecanase-1 is also a critical domain for substrate recognition and cleavage. It is these two domains that determine our classification of a novel aggrecanase family member. The protein sequence of the Aggrecanase-1 DNA sequence was used to query against the GeneBank ESTs focusing on human ESTs using TBLASTN. The resulting sequences were the starting point in the effort to identify full length sequence for potential family members. The nucleotide sequence of the aggrecanase of the present invention is comprised of one EST (AA588434) that contains homology over the catalytic domain and zinc binding motif of Aggrecanase-1 (ADAMTS4).

This human aggrecanase sequence was isolated from a dT-primed cDNA library constructed in the plasmid vector pED6-dpc2. cDNA was made from human testes RNA purchased from Clontech. The probe to isolate the aggrecanase of the present invention was generated from the sequence obtained from the database search. The sequence of the probe was as follows:

5'-GGTCAAATCGCGTCAGTGTAAATACGGG-3' (SEQ ID NO: 6). The DNA probe was radioactively labeled with $^{32}$P and used to screen the human testes dT-primed cDNA library, under high stringency hybridization/washing conditions, to identify clones containing sequences of the human candidate #8.

Fifty thousand library transformants were plated at a density of approximately 5000 transformants per plate on 10 plates. Nitrocellulose replicas of the transformed colonies were hybridized to the $^{32}$P labeled DNA probe in standard hybridization buffer (1×Blotto(25×Blotto=%5 nonfat dried milk, 0.02% azide in dH2O)+1% NP-40+6×SSC+0.05% Pyrophosphate) under high stringency conditions (65° C. for 2 hours shaking). After 2 hours hybridization, the radioactively labeled DNA probe containing hybridization solution was removed and the filters were washed under high stringency conditions (3×SSC, 0.05% Pyrophosphate for 5 minutes at RT; followed by 2.2×SSC, 0.05% Pyrophosphate for 15 minutes at RT; followed by 2.2×SSC, 0.05% Pyrophosphate for 1–2 minutes at 65° C.). The filters were wrapped in Saran wrap and exposed to X-ray film for overnight. The autoradiographs were developed and positively hybridizing transformants of various signal intensities were identified. These positive clones were picked; grown for 12 hours in selective medium(L-broth plus 100 μg/ml ampicillin) and plated at low density (approximately 100 colonies per plate). Nitrocellulose replicas of the colonies were hybridized to the $^{32}$P labeled probe in standard hybridization buffer ((1×Blotto (25×Blotto=%5 nonfat dried milk, 0.02% azide in dH2O)+ 1% NP-40+6×SSC+0.05% Pyrophosphate) under high stringency conditions (65° C. for 2 hours). After 2 hours hybridization, the radioactively labeled DNA probe containing hybridization solution was removed and the filters were washed under high stringency conditions (3×SSC, 0.05% Pyrophosphate for 5 minutes at RT; followed by 2.2×SSC, 0.05% Pyrophosphate for 15 minutes at RT; followed by 2.2×SSC, 0.05% Pyrophosphate for 1–2 minutes at 65° C.). The filters were wrapped in Saran wrap and exposed to X-ray film for overnight. The autoradiographs were developed and positively hybridizing transformants were identified. Bacterial stocks of purified hybridization positive clones were made and plasmid DNA was isolated. The sequence of the cDNA insert was determined and is set forth in SEQ ID NO: 1 from nucleotide #1086(TCG) through #3396(CGC). This sequence has been deposited in the American Type Culture Collection—10801 University Blvd. Manassas, Va. 20110-2209 USA as PTA-2284. The cDNA insert contained the sequences of the DNA probe used in the hybridization. The 5'(prime) and 3'(prime) sequences of this isolated sequence was then extracted using the RACE protocol. The fully determined sequence is set forth in SEQ ID NO: 1 from nucleotide #1 to #3766.

The human candidate #8 sequence obtained aligns with several ESTs in the public database. Candididate #8 shows homology with ADAMTS 7 and 6. The aggrecanase of the present invention contains the zinc binding signature region, a "MET turn", and tsp type-1 motif, however is missing the signal and propeptide regions and c-terminal spacer regions. It is with these criteria that candidate #8 is considered a novel Aggrecanase family member.

The aggrecanase sequence of the invention can be used to design probes for further screening for full length clones containing the isolated sequence.

The 5P (signal and propeptide) and 3P (C-terminal spacer regions) ends of the full-length version of EST8 were determined by RACE PCR using the Clontech Marathon cDNA Amplification Kit. The testes and stomach Marathon cDNA sources were used as substrates for the RACE reactions. 5P RACE primers used in the reactions were; GSP1— AGTCTAGAAAGCTGGTGATGTAGTCACGGC (SEQ ID NO: 7) and GSP2— TAGATGCATATGTCATAGCGTGTGATGAGCACTGC (SEQ ID NO: 8) (contains a NsiI site). The Advantage-2 PCR Kit from Clontech was used to set up nested RACE reactions following instructions in the user manual for the Marathon cDNA Amplification Kit; the amount the GSP primers used was 0.2 pmol/ul of each PCR primer/ul of reaction mix. GSP1 primer was used for the first round of PCR and GSP2 primer was used for the nested reaction. Products from the nested RACE reactions were digested with NsiI (on the GSP2 primer) and NotI (on the AP2 primer provided in the Clontech kit and used in the nested RACE PCR) and ligated into the CS2+ vector cut with NsiI and NotI. Ligated products were transformed into ElectroMAX DH10B cells from Life Technologies. Cloned RACE products were plated at low density (approximately 300 colonies per plate). Nitrocellulose replicas of the transformed colonies were hybridized to a $^{32}$P labeled DNA probe in standard hybridization buffer (1×Blotto (25×Blotto=5% nonfat dried milk, 0.02% azide), 1% NP-40, 6×SSC, 0.05% pyrophosphate) under high stringency conditions (65° C. for 2 hours shaking). Sequence at the 5P end of candidate 8-1 was used as a DNA probe: CTCGAGTCTGGGAAGCAC-CGTTAACATCC (SEQ ID NO: 9).

After 2 hours, the hybridization solution (hybridization buffer containing 1×10$^6$ cpm $^{32}$P labeled DNA probe) was removed and the filters were washed under high stringency conditions (3×SSC, 0.05% pyrophosphate for 5 minutes at RT standing; followed by 2.2×SSC, 0.05% pyrophosphate for 15 minutes shaking at RT; followed by 2.2×SSC, 0.05% pyrophosphate for 1–2 minutes shaking at 65° C.). The filters were covered with Saran Wrap and exposed to X-ray film overnight. The autoradiographs were developed and positively hybridizing transformants of various signal intensities were identified. These positive clones were picked and then grown for 12 hours in selective medium (L-broth plus 100 ug/ml ampicillin). Plasmid DNA was prepared and sent for DNA sequence analysis. A second round of hybridizations was performed using a probe that was made to sequence more 5P than candidate 8-1. The DNA probe sequence was deduced from the 5P RACE products. The second probe sequence was as follows: GAAGGCGATCT-CATAGCTCTCCAGACT (SEQ ID NO: 10). Cloned RACE products were again plated and the same hybridization protocol was followed, except using the more 5P probe. The initiator Met was deduced from a consensus sequence derived from the 5P RACE products generated from both the testes and the stomach cDNAs. 3P RACE primers used were; GSP1— GCTCTAGACTGGTCTGAGTGCACCCCCAGCT (SEQ ID NO: 11) and GSP2— GTCCTTTGCAAGAGCGCAGACCAC (SEQ ID NO: 12). The Advantage GC-2 PCR Kit from Clontech was used to set up nested RACE reactions. Reactions were set up following the instructions in the user manual for the Marathon cDNA Amplification Kit; with the exception that the amount of GC melt used was 5 ul per 50 ul reaction; the amount the GSP primers used was 0.2 pmol/ul of each PCR primer/ul of reaction mix. GSP1 primer was used for the first round of PCR and GSP2 primer was used for the nested reaction. Products from the nested RACE reactions were ligated into the pT-Adv vector using the AdvanTAge PCR Cloning Kit, per manufacturer's instructions. Ligated products were transformed into ElectroMAX DH10B cells from Life Technologies. Cloned RACE products were plated at low density (approximately 300 colonies per plate). Nitrocellulose replicas of the transformed colonies were hybridized to a $^{32}$P labeled DNA probe in standard hybridization buffer (1×Blotto (25×Blotto=5% nonfat dried milk, 0.02% azide), 1% NP-40, 6×SSC, 0.05% pyrophosphate) under high stringency conditions (65° C. for 2 hours shaking). Sequence at the 3P end of candidate 8-1 was used as a DNA probe: GCACTGTGCAGAGCACTCACCCCA (SEQ ID NO: 13). After 2 hours, the hybridization solution (hybridization buffer containing 1×10$^6$ cpm $^{32}$P labeled DNA probe) was removed and the filters were washed under high stringency conditions (3×SSC, 0.05% pyrophosphate for 5 minutes at RT standing; followed by 2.2×SSC, 0.05% pyrophosphate for 15 minutes shaking at RT; followed by 2.2×SSC, 0.05% pyrophosphate for 1–2 minutes shaking at 65° C.). The filters were covered with Saran Wrap and exposed to X-ray film overnight. The autoradiographs were developed and positively hybridizing transformants of various signal intensities were identified. The positive clones were picked and then grown for 12 hours in selective medium (L-broth plus 100 ug/ml ampicillin). Plasmid DNA was prepared and sent for DNA sequence analysis. The stop codon was deduced from a consensus sequence derived from the 3P RACE products generated from both the testes and the stomach cDNAs.

With the exception of the region from base pair 1332 to 1517(for this description base pair #1 is A of the initiator Met (ATG), the full-length sequence of EST8 was confirmed. A search of the public databases revealed a partial sequence for EST8, termed ADAMTS10. We used the sequence from this partial clone to construct the contiguous region of our EST8 (base pair 1332 to 1517) with synthetic oligonucleotides.

The full-length sequence for EST8 (SEQ ID NO: 3) was the consensus sequence derived from the hybridization positive candidate 8-1, the publicly available sequences representing EST8, and the PCR products from the Clontech testes and stomach cDNAs. The final EST8 expression construct was assembled from 4 EST8 specific fragments. The 5P portion of EST8, from base pair 1–1342, was PCR amplified from a pool of stomach and testes cDNAs and will be termed fragment 1. The following primers were used; 5P PCR primer—AAATGGGCGAATTCCCACCATGGCTC-CCGCCTGCCAGATCCTCCG (SEQ ID NO: 14) (contains an 8 base pair linker (AAATGGGC) an EcoRI cloning site (GAATTC) and a Kozak sequence (CCACC) upstream of the initiator Met) and 3P PCR primer—CCGAGTCTAGAAAGCTGGTGATGTAG (SEQ ID NO: 15) (contains an XbaI site (TCTAGA)). This PCR product was digested with EcoRI and XbaI using standard digestion conditions. The next portion of the gene, fragment 2, was constructed using synthetic oligonucleotides. The synthetic fragment stretched from an XbaI site to a BsrFI site representing base pair 1333 to 1517 of EST8. The synthetic oligonucleotides consisted of the following sequence: the top strand consisted of—CTAGACTCGGGCCTGGGGCTCTGCCTGAACA ACCGACCCCCCAGACAGGACT TTGTGTACCCGA-CAGTGGCACCGGGCCAAGCCTACGATG-CAGATGAGCAATG CCGCTTTCAGCATGGAGT-CAAATCGCGTCAGTGTAAATACGGGGAGGTCTGC AGCGAGCTGTGGTGTCTGAGCAAGAGCAA (SEQ ID NO: 16); the bottom strand consisted of—CCGGTTGCTCTTGCTCAGACACCACAGCTCG CTGCAGACCTCCCCGTATTTAC ACTGACGC-GATTTGACTCCATGCTGAAAGCGGCAT-TGCTCATCTGCATCGTAG GCTTGGCCCGGTGC-CACTGTCGGGTACACAAAGTCCTGTCTGGGGGGT CGGTT GTTCAGGCAGAGCCCCAGGCCCGAGT (SEQ ID NO: 17). The next portion of EST8, fragment 3, was a BsrFI to SphI fragment digested from candidate 8-1. This represented from base pair 1518 to 2783 of the full-length version of EST8. The 3P portion of EST8, termed fragment 4 (base pair 2663 to 3314), was PCR amplified. The following primers were used; 5P—GGGTTGTAGGGAACTGGTCGCTCTG (SEQ ID NO: 18) (located within fragment 3, upstream of the SphI site) and 3P—AAATGGGCCTCGAGCCCTAGTGGCCCTGGCA GGTTTTGC (SEQ ID NO: 19) (contains an 8 base pair linker (AAATGGGC) and a XhoI site (CTCGAG) downstream of the stop codon (TAG)). This PCR product was digested with SphI and XhoI using standard digestion conditions. A full-length version of EST8 was constructed by ligating these 4 described fragments, 5P fragment 1 (EcoRI/XbaI), internal fragment 2 (XbaI/BsrFI), internal fragment 3 (BsrFI/SphI), and 3P fragment 4 (SphI/XhoI) into the Cos expression vector pED6-dpc2 (digested with EcoRI and XhoI). The final construct had a mutation in the XhoI cloning site, which was destroyed in the ligation. This did not effect the EST8 coding sequence and was left in the construct.

Example 2

Expression of Aggrecanase

In order to produce murine, human or other mammalian aggrecanase-related proteins, the DNA encoding it is transferred into an appropriate expression vector and introduced into mammalian cells or other preferred eukaryotic or prokaryotic hosts including insect host cell culture systems by conventional genetic engineering techniques. Expression system for biologically active recombinant human aggrecanase is contemplated to be stably transformed mammalian cells, insect, yeast or bacterial cells.

One skilled in the art can construct mammalian expression vectors by employing the sequence of SEQ ID NO: 3 or the sequence of SEQ ID NO: 1 comprising nucleotide #1 to #3766 or comprising nuclotide #1086 to #3396 of SEQ ID NO: 1 or other DNA sequences encoding aggrecanase-related proteins or other modified sequences and known vectors, such as pCD (Okayama et al., *Mol. Cell Biol.*, 2:161–170 (1982)), pJL3, pJL4 (Gough et al., *EMBO J.*, 4:645–653 (1985)) and pMT2 CXM.

The mammalian expression vector pMT2 CXM is a derivative of p91023(b) (Wong et al., *Science* 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis (Morinaga, et al., *Biotechnology* 84: 636 (1984)). This removes bases 1075 to 1145 relative to the Hind III site near the SV40 origin of replication and enhancer sequences of pMT2. In addition it inserts the following sequence:

5'PO-CATGGGCAGCTCGAG-3'(SEQ ID NO: 20) at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E. coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR:

```
                                      (SEQ ID NO: 21)
5'-ctgcagGCGAGCCTgaattcctcgagCCATCatg-3'
        PstI              Eco RI XhoI
```

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 (S. K. Jung, et al., *J. Virol* 63:1651–1660 (1989) by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5'TaqI protruding end and a 3'XhoI protruding end which has the following sequence:

```
                                      (SEQ ID NO: 22)
5'-cgaGGTTAAAAAACGTCTAGGCCCCCCGAACCACGGGGACGTGGTTT
   TaqI TCCTTTGAAAAACACGattgc-3'
            XhoI
```

This sequence matches the EMC virus leader sequence from nucleotide 763 to 827. It also changes the ATG at position 10 within the EMC virus leader to an ATT and is followed by a XhoI site. A three way ligation of the pMT21 Eco RI-16hoI fragment, the EMC virus EcoRI-TaqI fragment, and the 68 bp oligonucleotide adapter TaqI-16hoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VAI gene, DHFR and β-lactamase markers and an EMC sequence, in appropriate relationships to direct the high level expression of the desired cDNA in mammalian cells.

The construction of vectors may involve modification of the aggrecanase-related DNA sequences. For instance, aggrecanase cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of aggrecanase-related proteins. Additionally, the sequence of SEQ ID NO: 3 or SEQ ID NO: 1 comprising nucleotide #1 to #3766 or comprising nuclotide #1086 to #3396 of SEQ ID NO: 1 or other sequences encoding aggrecanase-related proteins can be manipulated to express a mature aggrecanase-related protein by deleting aggrecanase encoding propeptide sequences and replacing them with sequences encoding the complete propeptides of other aggrecanase proteins.

One skilled in the art can manipulate the sequences of SEQ ID NO: 3 or SEQ ID NO: 1 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified aggrecanase-related coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and a aggrecanase-related protein expressed thereby. For a strategy for producing extracellular expression of aggrecanase-related proteins in bacterial cells, see, e.g. European patent application EP 177,343.

Similar manipulations can be performed for the construction of an insect vector (See, e.g. procedures described in published European patent application 155,476) for expression in insect cells. A yeast vector could also be constructed employing yeast regulatory sequences for intracellular or extracellular expression of the factors of the present invention by yeast cells. (See, e.g., procedures described in published PCT application WO 86/00639 and European patent application EP 123,289).

A method for producing high levels of a aggrecanase-related protein of the invention in mammalian, bacterial, yeast or insect host cell systems may involve the construction of cells containing multiple copies of the heterologous Aggrecanase-related gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for an aggrecanase-related protein of the invention in operative association with other plasmid sequences enabling expression thereof and the DHFR expression plasmid pAdA26SV (A)3 (Kaufman and Sharp, *Mol. Cell. Biol.*, 2:1304 (1982)) can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., *Mol Cell Biol.*, 5:1750 (1983). Transformants are cloned, and biologically active aggrecanase expression is monitored by the assays described above. Aggrecanase protein expression should increase with increasing levels of MTX resistance. Aggrecanase polypeptides are characterized using standard techniques known in the art such as pulse labeling with (35S) methionine or cysteine and polyacrylamide gel electrophoresis. Similar procedures can be followed to produce other related aggrecanase-related proteins.

In one example the aggrecanase gene of the present invention set forth in SEQ ID NO: 3 is cloned into the expression vector pED6 (Kaufman et al., Nucleic Acid Res. 19:4885–4490(1991)). COS and CHO DUKX B11 cells are transiently transfected with the aggrecanase sequence of the invention (+/− co-transfection of PACE on a separate pED6 plaasmid) by lipofection(LF2000, Invitrogen). Duplicate tranfections are performed for each gene of interest: (a) one for harvesting conditioned media for activity assay and (b) one for 35-S-methionine/cysteine metabolic labeling.

On day one media is changed to DME(COS) or alpha (CHO) media+1% heat-inactivated fetal calf serum+/−100 µg/ml heparin on wells(a) to be harvested for activity assay. After 48 h (day4), conditioned media is harvested for activity assay.

On day 3, the duplicate wells(b) were changed to MEM (methioone-free/cyysteine free) media+1% heat-inactivated fetal callf serum+100 µg/ml heparin+100 µCi/ml 35S-methioine/cysteine (Redivue Pro mix, Amersham). Following 6 h incubation at 37° C., conditioned media was harvested and run on SDS-PAGE gels under reducing conditions. Proteins are visualized by autoradiography.

Example 3

Biological Activity of Expressed Aggrecanase

To measure the biological activity of the expressed aggrecanase-related proteins obtained in Example 2 above, the proteins are recovered from the cell culture and purified by isolating the aggrecanase-related proteins from other proteinaceous materials with which they are co-produced as well as from other contaminants. The purified protein may be assayed in accordance with assays described above. Purification is carried out using standard techniques known to those skilled in the art.

Protein analysis is conducted using standard techniques such as SDS-PAGE acrylamide (Laemmli, *Nature* 227:680 (1970)) stained with silver (Oakley, et al. *Anal. Biochem.* 105:361 (1980)) and by immunoblot (Towbin, et al. *Proc. Natl. Acad. Sci. USA* 76:4350 (1979)).

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A purified aggrecanase polypeptide comprising the amino acid sequence of SEQ ID NO:4.

2. A purified aggrecanase polypeptide produced by the steps of (a) culturing a cell transformed with a DNA molecule comprising SEQ ID NO:3; and (b) recovering and purifying a polypeptide comprising the amino acid sequence set forth in SEQ ID NO:4.

* * * * *

UNITED STATES PATENT AND TRADEMARK OFFICE
CERTIFICATE OF CORRECTION

PATENT NO. : 6,689,599 B1
DATED : February 10, 2004
INVENTOR(S) : Racie et al.

It is certified that error appears in the above-identified patent and that said Letters Patent is hereby corrected as shown below:

Column 5,
Line 67, "leu" should read -- Leu --.

Signed and Sealed this

Twenty-third Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 6,689,599 B1　　　　　　　　　　　　　　　　　　　　　Page 1 of 1
APPLICATION NO. : 09/981953
DATED : February 10, 2004
INVENTOR(S) : Racie et al.

It is certified that error appears in the above-identified patent and that said Letters Patent is hereby corrected as shown below:

ON THE TITLE PAGE, PLEASE DELETE ITEM (75) AND INSERT ITEM (75) AS FOLLOWS:

Lisa A. Racie, Acton, MA (US);
Natalie C. Twine, Goffstown, NH (US);
Michael J. Agostino, Andover, MA (US); Edward R. LaVallie, Harvard, MA (US) Behany A. Freeman, Arlington, MA (US); Katy E. Georgiadis, Belmont, MA (US); Carl R. Flannery, Acton, MA (US); Weilan Zeng, Waltham, MA (US) Christopher J. Corcoran, Arlington, MA (US)

Signed and Sealed this

Sixteenth Day of December, 2008

JON W. DUDAS
*Director of the United States Patent and Trademark Office*

SEQUENCE LISTING

```
<160> NUMBER OF SEQ ID NOS: 22

<210> SEQ ID NO 1
<211> LENGTH: 3766
<212> TYPE: DNA
<213> ORGANISM: Unknown Organism
<220> FEATURE:
<223> OTHER INFORMATION: Description of Unknown Organism: Nucleotide
      sequence of the aggrecanase molecule

<400> SEQUENCE: 1
gcggccgctg aattctaggg aggccccggg cgcggcgcag gctccaaaga agaagaaacc        60
aaggcccaga gagggaggcc caggtgcagg gagcaggcga gggaaggatc cgtacagggg      120
cccaacacta ctccaccaac cgaagccccc aaaaggagcc cggtgatgct gcgaaggctg      180
tgaacagggg aggcggcact gtggggctg ccggcagccg gggctgggga gagacatgtg       240
gacacgtggc ctctatggct cccgcctgcc agatcctccg ctgggccctc gccctggggc      300
tgggcctcat gttcgaggtc acgcacgcct tccggtctca agatgagttc ctgtccagtc      360
tggagagcta tgagatcgcc ttccccaccc gcgtggacca caacggggca ctgctggcct      420
tctcgccacc tcctccccgg aggcagcgcc gcggcacggg ggccacagcc gagtcccgcc      480
tcttctacaa agtggcctcg cccagcaccc acttcctgct gaacctgacc cgcagctccc      540
gtctactggc agggcacgtc tccgtggagt actggacacg ggagggcctg gcctggcaga      600
gggcggcccg gccccactgc ctctacgctg gtcacctgca gggccaggcc agcagctccc      660
atgtggccat cagcacctgt ggaggcctgc acggcctgat cgtggcagac gaggaagagt      720
```

-continued

```
acctgattga gccctgcac ggtgggccca agggttctcg gagcccggag gaaagtggac    780
cacatgtggt gtacaagcgt tcctctctgc gtcaccccca cctggacaca gcctgtggag    840
tgagagatga gaaaccgtgg aaagggcggc catggtggct gcggaccttg aagccaccgc    900
ctgccaggcc cctggggaat gaaacagagc gtggccagcc aggcctgaag cgatcggtca    960
gccgagagcg ctacgtggag accctggtgg tggctgacaa gatgatggtg gcctatcacg   1020
ggcgccggga tgtggagcag tatgtcctgg ccatcatgaa cattgttgcc aaacttttcc   1080
aggactcgag tctgggaagc accgttaaca tcctcgtaac tcgcctcatc ctgctcacgg   1140
aggaccagcc cactctggag atcacccacc atgccgggaa gtccctggac agcttctgta   1200
agtggcagaa atccatcgtg aaccacagcg gccatggcaa tgccattcca gagaacggtg   1260
tggctaacca tgacacagca gtgctcatca cacgctatga catctgcatc tacaagaaca   1320
aaccctgcgg cacactaggc ctggcccggg tgggcggaat gtgtgagcgc gagagaagct   1380
gcagcgtcaa tgaggacatt ggcctggcca cagcgttcac cattgcccac gagatcgggc   1440
acacattcgg catgaaccat gacggcgtgg gaaacagctg tggggcccgt ggtcaggacc   1500
cagccaagct catggctgcc cacattacca tgaagaccaa cccattcgtg tggtcatcct   1560
gcagccgtga ctacatcacc agcttttctag actcagggcc tggggctctg cctgaacaac   1620
cggcccccca gacaggactt tgtgtacccg acagtggcac cgggccaagc ctacgatgca   1680
gatgagcaat gccgctttca gcatggagtc aaatcgcgtc agtgtaaata cgggaggtct   1740
gcagcgagct gtggtgtctg agcaagagca accggtgcat caccaacagc atcccggccg   1800
ccgagggcac gctgtgccag acgcacacca tcgacaaggg gtggtgctac aaacgggtct   1860
gtgtcccctt tgggtcgcgc ccagagggtg tggacggagc ctgggggccg tggactccat   1920
ggggcgactg cagccggacc tgtgcggcg cgtgtcctc ttctagccgt cactgcgaca   1980
gccccaggcc aaccatcggg ggcaagtact gtctgggtga gagaaggcgg caccgctcct   2040
gcaacacgga tgactgtccc cctggctccc aggacttcag agaagtgcag tgttctgaat   2100
ttgacagcat cccctttccgt gggaaattct acaagtgaa aacgtaccgg ggaggggcg   2160
tgaaggcctg ctcgctcacg tgcctagcgg aaggcttcaa cttctacacg gagagggcgg   2220
cagccgtggt ggacgggaca ccctgccgtc cagacacggt ggacatttgc gtcagtggcg   2280
aatgcaagca cgtgggctgc gaccgagtcc tgggctccga cctgcgggag gacaagtgcc   2340
gagtgtgtgg cggtgacggc agtgcctgcg agaccatcga gggcgtcttc agcccagcct   2400
cacctggggc cgggtacgag gatgtcgtct ggattcccaa aggctccgtc cacatcttca   2460
tccaggatct gaacctctct ctcagtcact tggccctgaa gggagaccag gagtccctgc   2520
tgctggaggg gctgcccggg acccccagc cccaccgtct gcctctagct gggaccacct   2580
ttcaactgcg acaggggcca gaccaggtcc agagcctcga agccctggga ccgattaatg   2640
catctctcat cgtcatggtg ctggcccgga ccgagctgcc tgccctccgc taccgcttca   2700
atgcccccat cgcccgtgac tcgctgcccc cctactcctg gcactatgcg ccctggacca   2760
agtgctcggc ccagtgtgca ggcggtagcc aggtgcaggc ggtggagtgc cgcaaccagc   2820
tggacagctc cgccggtcgcc cccactact gcagtgccca cagcaagctg cccaaaaggc   2880
agcgcgcctg caacacggag ccttgccctc cagactgggt tgtagggaac tggtcgctct   2940
gcagccgcag ctgcgatgca ggcgtgcgca ccgctcggt cgtgtgccag cgccgcgtct   3000
ctgccgcgga ggagaaggcg ctggacgaca gcgcatgccc gcagccgcgc ccacctgtac   3060
```

-continued

```
tggaggcctg ccacggcccc acttgccctc cggagtgggc ggccctcgac tggtctgagt      3120 gcaccccccag ctgcgggccg ggcctccgcc accgcgtggt cctttgcaag agcgcagacc    3180
accgcgccac gctgcccccg cgcactgct cacccgccgc caagccaccg gccaccatgc     3240
gctgcaactt gcgccgctgc ccccggccc gctgggtggc tggcgagtgg ggtgagtgct     3300
ctgcacagtg cggcgtcggg cagcggcagc gtcggtgcg ctgcaccagc cacacgggcc     3360
aggcgtcgca cgagtgcacg gaggccctgc ggccgcccac cacgcagcaa tgtgaggcca    3420
agtgcgacag cccaacccccc gggggcggcc ctgaagagtg caaggatgtg aacaaggtcg   3480
cctactgccc cctggtgctc aaatttcagt tctgcagccg agcctacttc cgccagatgt    3540
gctgcaaaac ctgccagggc cactagggggg cgcgcggcac ccggagccac agctggcggg   3600
gtctccgccg ccagtcctgc agcgggccgg ccagaggggg ccccgggggg cgggaactg     3660 ggagggaagg gtgagacgga gccggaagtt atttattggg aacccctgca gggccctggc    3720 tgggggatg gagagggct ggctatccac ctgcccgggc ggccgc                     3766
```

<210> SEQ ID NO 2
<211> LENGTH: 770
<212> TYPE: PRT
<213> ORGANISM: Unknown Organism
<220> FEATURE:
<223> OTHER INFORMATION: Description of Unknown Organism: Amino acid
      sequence of the aggrecanase molecule
<220> FEATURE:
<221> NAME/KEY: MOD_RES
<222> LOCATION: (200)
<223> OTHER INFORMATION: Any amino acid
<220> FEATURE:
<221> NAME/KEY: MOD_RES
<222> LOCATION: (214)
<223> OTHER INFORMATION: Any amino acid

<400> SEQUENCE: 2

```
Ser Ser Leu Gly Ser Thr Val Asn Ile Leu Val Thr Arg Leu Ile Leu
 1               5                  10                  15

Leu Thr Glu Asp Gln Pro Thr Leu Glu Ile Thr His His Ala Gly Lys
            20                  25                  30

Ser Leu Asp Ser Phe Cys Lys Trp Gln Lys Ser Ile Val Asn His Ser
        35                  40                  45

Gly His Gly Asn Ala Ile Pro Glu Asn Gly Val Ala Asn His Asp Thr
    50                  55                  60

Ala Val Leu Ile Thr Arg Tyr Asp Ile Cys Ile Tyr Lys Asn Lys Pro
65                  70                  75                  80

Cys Gly Thr Leu Gly Leu Ala Pro Val Gly Gly Met Cys Glu Arg Glu
                85                  90                  95

Arg Ser Cys Ser Val Asn Glu Asp Ile Gly Leu Ala Thr Ala Phe Thr
            100                 105                 110

Ile Ala His Glu Ile Gly His Thr Phe Gly Met Asn His Asp Gly Val
        115                 120                 125

Gly Asn Ser Cys Gly Ala Arg Gly Gln Asp Pro Ala Lys Leu Met Ala
    130                 135                 140

Ala His Ile Thr Met Lys Thr Asn Pro Phe Val Trp Ser Ser Cys Ser
145                 150                 155                 160

Arg Asp Tyr Ile Thr Ser Phe Leu Asp Ser Gly Pro Gly Ala Leu Pro
                165                 170                 175

Glu Gln Pro Ala Pro Gln Thr Gly Leu Cys Val Pro Asp Ser Gly Thr
            180                 185                 190
```

-continued

```
Gly Pro Ser Leu Arg Cys Arg Xaa Ala Met Pro Leu Ser Ala Trp Ser
        195                 200                 205

Gln Ile Ala Ser Val Xaa Ile Arg Glu Val Cys Ser Glu Leu Trp Cys
        210                 215                 220

Leu Ser Lys Ser Asn Arg Cys Ile Thr Asn Ser Ile Pro Ala Ala Glu
225                 230                 235                 240

Gly Thr Leu Cys Gln Thr His Thr Ile Asp Lys Gly Trp Cys Tyr Lys
                245                 250                 255

Arg Val Cys Val Pro Phe Gly Ser Arg Pro Glu Gly Val Asp Gly Ala
                260                 265                 270

Trp Gly Pro Trp Thr Pro Trp Gly Asp Cys Ser Arg Thr Cys Gly Gly
            275                 280                 285

Gly Val Ser Ser Ser Arg His Cys Asp Ser Pro Arg Pro Thr Ile
        290                 295                 300

Gly Gly Lys Tyr Cys Leu Gly Glu Arg Arg His Arg Ser Cys Asn
305                 310                 315                 320

Thr Asp Asp Cys Pro Pro Gly Ser Gln Asp Phe Arg Glu Val Gln Cys
                325                 330                 335

Ser Glu Phe Asp Ser Ile Pro Phe Arg Gly Lys Phe Tyr Lys Trp Lys
                340                 345                 350

Thr Tyr Arg Gly Gly Val Lys Ala Cys Ser Leu Thr Cys Leu Ala
        355                 360                 365

Glu Gly Phe Asn Phe Tyr Thr Glu Arg Ala Ala Ala Val Val Asp Gly
        370                 375                 380

Thr Pro Cys Arg Pro Asp Thr Val Asp Ile Cys Val Ser Gly Glu Cys
385                 390                 395                 400

Lys His Val Gly Cys Asp Arg Val Leu Gly Ser Asp Leu Arg Glu Asp
                405                 410                 415

Lys Cys Arg Val Cys Gly Gly Asp Gly Ser Ala Cys Glu Thr Ile Glu
                420                 425                 430

Gly Val Phe Ser Pro Ala Ser Pro Gly Ala Gly Tyr Glu Asp Val Val
        435                 440                 445

Trp Ile Pro Lys Gly Ser Val His Ile Phe Ile Gln Asp Leu Asn Leu
        450                 455                 460

Ser Leu Ser His Leu Ala Leu Lys Gly Asp Gln Glu Ser Leu Leu Leu
465                 470                 475                 480

Glu Gly Leu Pro Gly Thr Pro Gln Pro His Arg Leu Pro Leu Ala Gly
                485                 490                 495

Thr Thr Phe Gln Leu Arg Gln Gly Pro Asp Gln Val Gln Ser Leu Glu
                500                 505                 510

Ala Leu Gly Pro Ile Asn Ala Ser Leu Ile Val Met Val Leu Ala Arg
        515                 520                 525

Thr Glu Leu Pro Ala Leu Arg Tyr Arg Phe Asn Ala Pro Ile Ala Arg
        530                 535                 540

Asp Ser Leu Pro Pro Tyr Ser Trp His Tyr Ala Pro Trp Thr Lys Cys
545                 550                 555                 560

Ser Ala Gln Cys Ala Gly Gly Ser Gln Val Gln Ala Val Glu Cys Arg
                565                 570                 575

Asn Gln Leu Asp Ser Ser Ala Val Ala Pro His Tyr Cys Ser Ala His
                580                 585                 590

Ser Lys Leu Pro Lys Arg Gln Arg Ala Cys Asn Thr Glu Pro Cys Pro
        595                 600                 605

Pro Asp Trp Val Val Gly Asn Trp Ser Leu Cys Ser Arg Ser Cys Asp
```

```
           610               615               620
Ala Gly Val Arg Ser Arg Ser Val Val Cys Gln Arg Val Ser Ala
625               630               635               640

Ala Glu Glu Lys Ala Leu Asp Asp Ser Ala Cys Pro Gln Pro Arg Pro
                645               650               655

Pro Val Leu Glu Ala Cys His Gly Pro Thr Cys Pro Pro Glu Trp Ala
                660               665               670

Ala Leu Asp Trp Ser Glu Cys Thr Pro Ser Cys Gly Pro Gly Leu Arg
                675               680               685

His Arg Val Val Leu Cys Lys Ser Ala Asp His Arg Ala Thr Leu Pro
                690               695               700

Pro Ala His Cys Ser Pro Ala Ala Lys Pro Pro Ala Thr Met Arg Cys
705               710               715               720

Asn Leu Arg Arg Cys Pro Pro Ala Arg Trp Val Ala Gly Glu Trp Gly
                725               730               735

Glu Cys Ser Ala Gln Cys Gly Val Gly Gln Arg Gln Arg Ser Val Arg
                740               745               750

Cys Thr Ser His Thr Gly Gln Ala Ser His Glu Cys Thr Glu Ala Leu
                755               760               765

Arg Pro
    770

<210> SEQ ID NO 3
<211> LENGTH: 3377
<212> TYPE: DNA
<213> ORGANISM: Unknown Organism
<220> FEATURE:
<223> OTHER INFORMATION: Description of Unknown Organism: Nucleotide
      sequence of the aggrecanase molecule

<400> SEQUENCE: 3
gaattcccac catggctccc gcctgccaga tcctccgctg ggccctcgcc ctggggctgg      60
gcctcatgtt cgaggtcacg cacgccttcc ggtctcaaga tgagttcctg tccagtctgg     120
agagctatga gatcgccttc cccacccgcg tggaccacaa cggggcactg ctggccttct     180
cgccacctcc tccccggagg cagcgccgcg gcacggggc  cacagccgag tcccgcctct     240
tctacaaagt ggcctcgccc agcacccact tcctgctgaa cctgacccgc agctcccgtc     300
tactggcagg gcacgtctcc gtggagtact ggacacggga gggcctggcc tggcagagag     360
cggcccggcc ccactgcctc tacgctggtc acctgcaggg ccaggccagc agctcccatg     420
tggccatcag cacctgtgga ggcctgcacg gcctgatcgt ggcagacgag gaagagtacc     480
tgattgagcc cctgcacggt gggcccaagg gttctcggag cccggaggaa agtggaccac     540
atgtggtgta caagcgttcc tctctgcgtc accccacct  ggacacagcc tgtggagtga     600
gagatgagaa accgtggaaa gggcggccat ggtggctgcg gaccttgaag ccaccgcctg     660
ccaggcccct gggaatgaa  acagagcgtg gccagccagg cctgaagcga tcggtcagcc     720
gagagcgcta cgtggagacc ctggtggtgg ctgacaagat gatggtggcc atcacgggc     780 gccgggatgt ggagcagtat gtcctggcca tcatgaacat tgttgccaaa cttttccagg     840
actcgagtct gggaagcacc gttaacatcc tcgtaactcg cctcatcctg ctcacggagg     900
accagcccac tctggagatc acccaccatg ccgggaagtc cctggacagc ttctgtaagt     960
ggcagaaatc catcgtgaac cacagcggtc atggcaatgc cattccagag aacggtgtgg    1020
ctaaccatga cacagcagtg ctcatcacac gctatgacat ctgcatctac aagaacaaac    1080
```

```
cctgcggcac actaggcctg gccccggtgg gcggaatgtg tgagcgcgag agaagctgca   1140
gcgtcaatga ggacattggc ctggccacag cgttcaccat tgcccacgag atcgggcaca   1200
cattcggcat gaaccatgac ggcgtgggaa acagctgtgg ggcccgtggt caggacccag   1260
ccaagctcat ggctgcccac attaccatga agaccaaccc gttcgtgtgg tcatcctgca   1320
gccgtgacta catcaccagc tttctagact cgggcctggg gctctgcctg aacaaccgac   1380
cccccagaca ggactttgtg tacccgacag tggcaccggg ccaagcctac gatgcagatg   1440
agcaatgccg ctttcagcat ggagtcaaat cgcgtcagtg taaatacggg gaggtctgca   1500
gcgagctgtg gtgtctgagc aagagcaacc ggtgcatcac caacagcatc ccggccgccg   1560
agggcacgct gtgccagacg cacaccatcg acaaggggtg gtgctacaaa cgggtctgtg   1620
tcccctttgg gtcgcgccca gagggtgtgg acggagcctg ggggccgtgg actccatggg   1680
gcgactgcag ccggacctgt ggcggcggcg tgtcctcttc tagccgtcac tgcgacagcc   1740
ccaggccaac catcggggc aagtactgtc tgggtgagag aaggcggcac cgctcctgca   1800
acacggatga ctgtccccct ggctcccagg acttcagaga agtgcagtgt tctgaatttg   1860
acagcatccc tttccgtggg aaattctaca agtggaaaac gtaccgggga gggggcgtga   1920
aggcctgctc gctcacgtgc ctagcggaag gcttcaactt ctacacggag agggcggcag   1980
ccgtggtgga cgggacaccc tgccgtccag acacggtgga catttgcgtc agtggcgaat   2040
gcaagcacgt gggctgcgac cgagtcctgg gctccgacct gcgggaggac aagtgccgag   2100
tgtgtggcgg tgacggcagt gcctgcgaga ccatcgaggg cgtcttcagc ccagcctcac   2160
ctggggccgg gtacgaggat gtcgtctgga ttcccaaagg ctccgtccac atcttcatcc   2220
aggatctgaa cctctctctc agtcacttgg ccctgaaggg agaccaggag tccctgctgc   2280
tggaggggct gcccgggacc ccccagcccc accgtctgcc tctagctggg accaccttc    2340
aactgcgaca ggggccagac caggtccaga gcctcgaagc cctgggaccg attaatgcat   2400
ctctcatcgt catggtgctg gcccggaccg agctgcctgc cctccgctac cgcttcaatg   2460
cccccatcgc ccgtgactcg ctgccccct actcctggca ctatgcgccc tggaccaagt   2520
gctcggccca gtgtgcaggc ggtagccagg tgcaggcggt ggagtgccgc aaccagctgg   2580
acagctccgc ggtcgccccc cactactgca gtgcccacag caagctgccc aaaaggcagc   2640
gcgcctgcaa cacggagcct tgccctccag actgggttgt agggaactgg tcgctctgca   2700
gccgcagctg cgatgcaggc gtgcgcagcc gctcggtcgt gtgccagcgc cgcgtctctg   2760
ccgcggagga gaaggcgctg gacgacagcg catgcccgca gccgcgccca cctgtactgg   2820
aggcctgcca cggccccact tgccctccgg agtgggcggc cctcgactgg tctgagtgca   2880
cccccagttg cgggccgggc ctccgccacc gcgtggtcct ttgcaagagc gcagaccacc   2940
gcgccacgct gccccccggcg cactgctcac ccgccgccaa gccaccggcc accatgcgct   3000
gcaacttgcg ccgctgcccc ccggcccgct gggtggctgg cgagtggggt gagtgctctg   3060
cacagtgcgg cgtcgggcag cggcagcgct cggtgcgctg caccagccac acgggccagg   3120
cgtcgcacga gtgcacggag gccctgcggc cgcccaccac gcagcagtgt gaggccaagt   3180
gcgacagccc aaccccggg gacggccctg aagagtgcaa ggatgtgaac aaggtcgcct   3240
actgcccct ggtgctcaaa tttcagttct gcagccgagc ctacttccgc cagatgtgct   3300
gcaaaacctg ccaggccac tagggtcgag gcccatttaa gccgaattct gcagatatcc   3360
atcacactgg cggccgc                                                   3377
```

-continued

```
<210> SEQ ID NO 4
<211> LENGTH: 1104
<212> TYPE: PRT
<213> ORGANISM: Unknown Organism
<220> FEATURE:
<223> OTHER INFORMATION: Description of Unknown Organism: Amino acid
      sequence of the aggrecanase molecule
<220> FEATURE:
<221> NAME/KEY: MOD_RES
<222> LOCATION: (1104)
<223> OTHER INFORMATION: Any amino acid

<400> SEQUENCE: 4

Met Ala Pro Ala Cys Gln Ile Leu Arg Trp Ala Leu Ala Leu Gly Leu
 1               5                  10                  15

Gly Leu Met Phe Glu Val Thr His Ala Phe Arg Ser Gln Asp Glu Phe
            20                  25                  30

Leu Ser Ser Leu Glu Ser Tyr Glu Ile Ala Phe Pro Thr Arg Val Asp
        35                  40                  45

His Asn Gly Ala Leu Leu Ala Phe Ser Pro Pro Pro Arg Arg Gln
    50                  55                  60

Arg Arg Gly Thr Gly Ala Thr Ala Glu Ser Arg Leu Phe Tyr Lys Val
65                  70                  75                  80

Ala Ser Pro Ser Thr His Phe Leu Leu Asn Leu Thr Arg Ser Ser Arg
                85                  90                  95

Leu Leu Ala Gly His Val Ser Val Glu Tyr Trp Thr Arg Glu Gly Leu
            100                 105                 110

Ala Trp Gln Arg Ala Ala Arg Pro His Cys Leu Tyr Ala Gly His Leu
        115                 120                 125

Gln Gly Gln Ala Ser Ser His Val Ala Ile Ser Thr Cys Gly Gly
    130                 135                 140

Leu His Gly Leu Ile Val Ala Asp Glu Glu Tyr Leu Ile Glu Pro
145                 150                 155                 160

Leu His Gly Gly Pro Lys Gly Ser Arg Ser Pro Glu Glu Ser Gly Pro
                165                 170                 175

His Val Val Tyr Lys Arg Ser Ser Leu Arg His Pro His Leu Asp Thr
            180                 185                 190

Ala Cys Gly Val Arg Asp Glu Lys Pro Trp Lys Gly Arg Pro Trp Trp
        195                 200                 205

Leu Arg Thr Leu Lys Pro Pro Pro Ala Arg Pro Leu Gly Asn Glu Thr
    210                 215                 220

Glu Arg Gly Gln Pro Gly Leu Lys Arg Ser Val Ser Arg Glu Arg Tyr
225                 230                 235                 240

Val Glu Thr Leu Val Val Ala Asp Lys Met Met Val Ala Tyr His Gly
                245                 250                 255

Arg Arg Asp Val Glu Gln Tyr Val Leu Ala Ile Met Asn Ile Val Ala
            260                 265                 270

Lys Leu Phe Gln Asp Ser Ser Leu Gly Ser Thr Val Asn Ile Leu Val
        275                 280                 285

Thr Arg Leu Ile Leu Leu Thr Glu Asp Gln Pro Thr Leu Glu Ile Thr
    290                 295                 300

His His Ala Gly Lys Ser Leu Asp Ser Phe Cys Lys Trp Gln Lys Ser
305                 310                 315                 320

Ile Val Asn His Ser Gly His Gly Asn Ala Ile Pro Glu Asn Gly Val
                325                 330                 335

Ala Asn His Asp Thr Ala Val Leu Ile Thr Arg Tyr Asp Ile Cys Ile
            340                 345                 350
```

```
Tyr Lys Asn Lys Pro Cys Gly Thr Leu Gly Leu Ala Pro Val Gly Gly
            355                 360                 365

Met Cys Glu Arg Glu Arg Ser Cys Ser Val Asn Glu Asp Ile Gly Leu
    370                 375                 380

Ala Thr Ala Phe Thr Ile Ala His Glu Ile Gly His Thr Phe Gly Met
385                 390                 395                 400

Asn His Asp Gly Val Gly Asn Ser Cys Gly Ala Arg Gly Gln Asp Pro
                405                 410                 415

Ala Lys Leu Met Ala Ala His Ile Thr Met Lys Thr Asn Pro Phe Val
            420                 425                 430

Trp Ser Ser Cys Ser Arg Asp Tyr Ile Thr Ser Phe Leu Asp Ser Gly
            435                 440                 445

Leu Gly Leu Cys Leu Asn Asn Arg Pro Pro Arg Gln Asp Phe Val Tyr
    450                 455                 460

Pro Thr Val Ala Pro Gly Gln Ala Tyr Asp Ala Asp Glu Gln Cys Arg
465                 470                 475                 480

Phe Gln His Gly Val Lys Ser Arg Gln Cys Lys Tyr Gly Glu Val Cys
                485                 490                 495

Ser Glu Leu Trp Cys Leu Ser Lys Ser Asn Arg Cys Ile Thr Asn Ser
            500                 505                 510

Ile Pro Ala Ala Glu Gly Thr Leu Cys Gln Thr His Thr Ile Asp Lys
            515                 520                 525

Gly Trp Cys Tyr Lys Arg Val Cys Val Pro Phe Gly Ser Arg Pro Glu
            530                 535                 540

Gly Val Asp Gly Ala Trp Gly Pro Trp Thr Pro Trp Gly Asp Cys Ser
545                 550                 555                 560

Arg Thr Cys Gly Gly Gly Val Ser Ser Ser Arg His Cys Asp Ser
                565                 570                 575

Pro Arg Pro Thr Ile Gly Gly Lys Tyr Cys Leu Gly Glu Arg Arg Arg
            580                 585                 590

His Arg Ser Cys Asn Thr Asp Asp Cys Pro Pro Gly Ser Gln Asp Phe
            595                 600                 605

Arg Glu Val Gln Cys Ser Glu Phe Asp Ser Ile Pro Phe Arg Gly Lys
    610                 615                 620

Phe Tyr Lys Trp Lys Thr Tyr Arg Gly Gly Gly Val Lys Ala Cys Ser
625                 630                 635                 640

Leu Thr Cys Leu Ala Glu Gly Phe Asn Phe Tyr Thr Glu Arg Ala Ala
                645                 650                 655

Ala Val Val Asp Gly Thr Pro Cys Arg Pro Asp Thr Val Asp Ile Cys
                660                 665                 670

Val Ser Gly Glu Cys Lys His Val Gly Cys Asp Arg Val Leu Gly Ser
            675                 680                 685

Asp Leu Arg Glu Asp Lys Cys Arg Val Cys Gly Gly Asp Gly Ser Ala
            690                 695                 700

Cys Glu Thr Ile Glu Gly Val Phe Ser Pro Ala Ser Pro Gly Ala Gly
705                 710                 715                 720

Tyr Glu Asp Val Val Trp Ile Pro Lys Gly Ser Val His Ile Phe Ile
                725                 730                 735

Gln Asp Leu Asn Leu Ser Leu Ser His Leu Ala Leu Lys Gly Asp Gln
            740                 745                 750

Glu Ser Leu Leu Leu Glu Gly Leu Pro Gly Thr Pro Gln Pro His Arg
            755                 760                 765
```

-continued

```
Leu Pro Leu Ala Gly Thr Thr Phe Gln Leu Arg Gln Gly Pro Asp Gln
    770                 775                 780
Val Gln Ser Leu Glu Ala Leu Gly Pro Ile Asn Ala Ser Leu Ile Val
785                 790                 795                 800
Met Val Leu Ala Arg Thr Glu Leu Pro Ala Leu Arg Tyr Arg Phe Asn
                805                 810                 815
Ala Pro Ile Ala Arg Asp Ser Leu Pro Pro Tyr Ser Trp His Tyr Ala
                820                 825                 830
Pro Trp Thr Lys Cys Ser Ala Gln Cys Ala Gly Gly Ser Gln Val Gln
            835                 840                 845
Ala Val Glu Cys Arg Asn Gln Leu Asp Ser Ser Ala Val Ala Pro His
        850                 855                 860
Tyr Cys Ser Ala His Ser Lys Leu Pro Lys Arg Gln Arg Ala Cys Asn
865                 870                 875                 880
Thr Glu Pro Cys Pro Pro Asp Trp Val Val Gly Asn Trp Ser Leu Cys
                885                 890                 895
Ser Arg Ser Cys Asp Ala Gly Val Arg Ser Arg Ser Val Val Cys Gln
                900                 905                 910
Arg Arg Val Ser Ala Ala Glu Glu Lys Ala Leu Asp Asp Ser Ala Cys
            915                 920                 925
Pro Gln Pro Arg Pro Pro Val Leu Glu Ala Cys His Gly Pro Thr Cys
    930                 935                 940
Pro Pro Glu Trp Ala Ala Leu Asp Trp Ser Glu Cys Thr Pro Ser Cys
945                 950                 955                 960
Gly Pro Gly Leu Arg His Arg Val Val Leu Cys Lys Ser Ala Asp His
                965                 970                 975
Arg Ala Thr Leu Pro Pro Ala His Cys Ser Pro Ala Ala Lys Pro Pro
                980                 985                 990
Ala Thr Met Arg Cys Asn Leu Arg Arg Cys Pro Pro Ala Arg Trp Val
            995                 1000                1005
Ala Gly Glu Trp Gly Glu Cys Ser Ala Gln Cys Gly Val Gly Gln Arg
    1010                1015                1020
Gln Arg Ser Val Arg Cys Thr Ser His Thr Gly Gln Ala Ser His Glu
1025                1030                1035                1040
Cys Thr Glu Ala Leu Arg Pro Thr Thr Gln Cys Glu Ala Lys
                1045                1050                1055
Cys Asp Ser Pro Thr Pro Gly Asp Gly Pro Glu Glu Cys Lys Asp Val
            1060                1065                1070
Asn Lys Val Ala Tyr Cys Pro Leu Val Leu Lys Phe Gln Phe Cys Ser
        1075                1080                1085
Arg Ala Tyr Phe Arg Gln Met Cys Cys Lys Thr Cys Gln Gly His Xaa
    1090                1095                1100

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      zinc binding signature sequence

<400> SEQUENCE: 5

Thr Ala Ala His Glu Leu Gly His Val Lys Phe
 1               5                  10

<210> SEQ ID NO 6
```

```
<211> LENGTH: 28
<212> TYPE: DNA
<213> ORGANISM: Artificial Sequence
<220> FEATURE:
<223> OTHER INFORMATION: Description of Artificial Sequence: Probe

<400> SEQUENCE: 6
ggtcaaatcg cgtcagtgta aatacggg                                              28

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 7
agtctagaaa gctggtgatg tagtcacggc                                            30

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 8
tagatgcata tgtcatagcg tgtgatgagc actgc                                      35

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Probe

<400> SEQUENCE: 9
ctcgagtctg ggaagcaccg ttaacatcc                                             29

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Probe

<400> SEQUENCE: 10
gaaggcgatc tcatagctct ccagact                                               27

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 11
gctctagact ggtctgagtg caccccagc t                                           31

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 12
```

```
gtcctttgca agagcgcaga ccac                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 13
gcactgtgca gagcactcac ccca                                              24

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 14
aaatgggcga attcccacca tggctcccgc ctgccagatc ctccg                       45

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 15
ccgagtctag aaagctggtg atgtag                                            26

<210> SEQ ID NO 16
<211> LENGTH: 185
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctagactcgg gcctggggct ctgcctgaac aaccgacccc ccagacagga ctttgtgtac       60
ccgacagtgg caccgggcca agcctacgat gcagatgagc aatgccgctt tcagcatgga     120
gtcaaatcgc gtcagtgtaa atacggggag gtctgcagcg agctgtggtg tctgagcaag     180
agcaa                                                                 185

<210> SEQ ID NO 17
<211> LENGTH: 185
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccggttgctc ttgctcagac accacagctc gctgcagacc tccccgtatt tacactgacg       60
cgatttgact ccatgctgaa agcggcattg ctcatctgca tcgtaggctt ggcccggtgc     120
cactgtcggg tacacaaagt cctgtctggg gggtcggttg ttcaggcaga gccccaggcc     180
cgagt                                                                 185

<210> SEQ ID NO 18
```

```
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 18
gggttgtagg gaactggtcg ctctg                                          25

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 19
aaatgggcct cgagccctag tggccctggc aggttttgc                           39

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
catgggcagc tcgag                                                     15

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctgcaggcga gcctgaattc ctcgagccat catg                                34

<210> SEQ ID NO 22
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgaggttaaa aaacgtctag gccccccgaa ccacggggac gtggttttcc tttgaaaaac    60
acgattgc                                                             68
```